US006388151B1

(12) United States Patent
Sullivan et al.

(10) Patent No.: US 6,388,151 B1
(45) Date of Patent: May 14, 2002

(54) SYNTHESIS OF TETRAALKYLCYCLOPENTADIENES

(75) Inventors: Jeffrey M. Sullivan, Loveland; Richard D. Crawford, Longmont, both of CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

(21) Appl. No.: 09/198,514

(22) Filed: Nov. 24, 1998

(51) Int. Cl.⁷ .............................. C07C 1/20; C07C 1/26; C07C 13/15; C07C 22/00; C07C 27/00; C07C 29/00; C07C 33/02
(52) U.S. Cl. .................. 585/318; 585/350; 585/357; 585/358; 585/359; 585/310; 585/317; 570/200; 570/186; 570/189; 570/226; 570/227; 570/228; 568/891; 568/892; 568/893; 568/894
(58) Field of Search ................................. 585/350, 357, 585/358, 359, 310, 317, 318; 510/200, 186, 189, 226, 227, 228; 568/891, 892, 893, 894

(56) References Cited

U.S. PATENT DOCUMENTS 5,329,056 A * 7/1994 Belmont ..................... 585/358

OTHER PUBLICATIONS

Advance Organic Chemistry textbook; Caery et al; p. 378, 1991.*
Organic Chemistry textbook; Solomon; pp. 692–701,1988.*
Halogenated Products of 1,2–Dichloroethylene Dimer and Their Transformations; Zapol'skii,1993.*
Improved Preparation of DI–Alpha.–Phenylbutyric Anhydride and Vinyl Bromide; Wang, 1986.*

* cited by examiner

Primary Examiner—Thuan D. Dang
(74) Attorney, Agent, or Firm—Edward S. Irons

(57) ABSTRACT

A method for synthesizing tetramethylcyclopentadiene from 2,3-dibromobutane is described. A 2-bromo-2-butene Grignard is reacted with an ethyl formate to produce a 3,5-dimethyl-2,5-heptadiene-4-ol magnesium bromide which is then quenched with acetic acid to produce 3,5-dimethyl-2, 5-hepadiene-4-ol.

11 Claims, No Drawings

SYNTHESIS OF TETRAALKYLCYCLOPENTADIENES

FIELD OF THE INVENTION

This invention relates to the synthesis of alkylcyclopentadienes. More particularly the invention relates to the synthesis of tetramethylcyclopentadiene (TMCp).

BACKGROUND OF THE INVENTION

U.S. Pat. Nos. 5,817,849 and 5,470,993 describe various metal complex addition polymerization catalysts and catalyst precursors which may be derived from TMCp.

Garner, *Tetrahedron Letters* (1994) 16:2463–2464 reports an overall 36% yield of TMCp from 2-butyne. Divinylcarbinol cyclodehydration to produce TMCp is described in U.S. Pat. No. 5,329,056.

SUMMARY OF THE INVENTION

Pursuant to the invention, 2-bromo-2-butene is produced in good yield by reaction of 2,3-dibromobutane with methanolic sodium hydroxide. Reaction of a Grignard derived from the 2-bromo-2-butene with ethyl formate yields 3,5-dimethyl-2,5-heptadiene-4-ol magnesium bromide, which is quenched with aqueous acetic acid to produce 3,5-dimethyl-2,5-heptadiene-4-ol (divinylcarbinol). TMCp for synthesis of addition polymerization catalysts is produced by cyclodehydration of divinyl alcohol with aqueous hydrochloric acid and ether, followed by caustic treatment to remove chlorotetramethylcyclopentene and sodium bromide.

Under appropriate conditions, an overall (distilled) TMCp yield of 50% to 75% from dibromobutane may be observed.

DETAILED DESCRIPTION OF THE INVENTION

The TMCP synthesis of the invention may include four steps as illustrated by laboratory Examples I to IV and by the description of a pilot plant embodiment.

I. LABORATORY EXAMPLES

All concentrations are in weight percent unless otherwise stated.

Step 1: Reaction of 2,3-dibromobutane with methanolic NaOH to produce 2-bromo-2-butene.

Example I

A 1 L 3-neck round bottom (RB) flask is charged with 1.2 moles of NaOH. Methanol (100 g) is added. An exothermic reaction provides a slurry of NaOH in NaOMe and methanol. The reaction proceeds with cooling such that the exotherm warms the reaction mixture to 40° to 45° C. 2,3-dibromobutane (1.0 mole) is added slowly at 35° C. over one hour. The reaction mixture is heated to 55–60° C. with vigorous stirring for 1–2 hours, and then cooled to 20° C. 190 g of 5% aqueous HCl is added. The mixture is allowed to settle for 30 minutes and to separate into an aqueous phase and an organic phase which contains 2-bromo-2-butene. The organic phase is separated and washed with 5% aqueous NaHCO$_3$ and dried over Na$_2$SO$_4$ (2 g). Solids are separated by filtration. The yield of 2-bromo-2-butene from 2,3-dibromobutane is 93%. The reaction is generally illustrated by Equation 1:

Equation 1

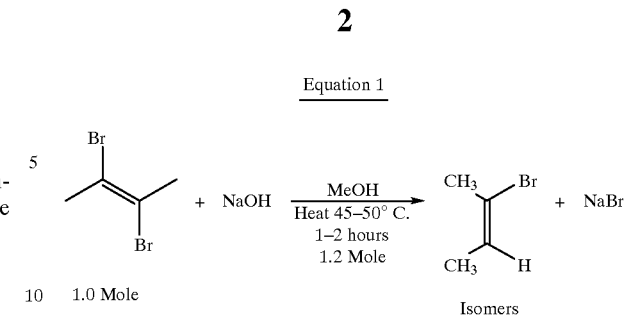

As Equation 1 indicates, the reaction is appropriately conducted by heating at a temperature of 55° C. to 60° C. for one to two hours. The methanolic sodium hydroxide slurry may contain from about 30% to about 60% sodium hydroxide. Potassium or lithium hydroxide may be used instead of sodium hydroxide. Any alkanol having 1 to 4 carbon atoms may be substituted for methanol.

2-bromo-2-butene may optionally be prepared by reacting 2,3-dibromobutane with 30% to 60%, preferably 50%, aqueous potassium hydroxide in the presence of benzyl alkyl ammonium chloride, preferably benzyl methyl ammonium chloride. The reaction may be conducted by refluxing at 70° C. to 110° C. for 2 to 7 hours.

Sodium or lithium hydroxide may be used instead of potassium hydroxide. The benzyl alkyl ammonium chloride may be used in a mol ratio of 0.05 to 2, preferably 0.1 to 0.5, with respect to the 2,3-dibromobutane. Any benzyl alkyl ammonium chloride having a one to five carbon atom alkyl group may be used.

Step 2: Conversion of 2-bromo-2-butene into 2-butenyl magnesium bromide.

Example II

A 1 L 3-neck flask was charged with Mg (1.1 mol, 26.7 g) and THF (400 ml, 352 g). 2-bromo-2-butene (135 g, 1 mol) was added. The reaction proceeded as the mixture was slowly warmed to 40° C. Upon apparent completion of the reaction, the mixture was allowed to settle at 40° C. for 30 minutes.

The supernatant which contained 2-butenyl magnesium bromide was cannulated to a 1 L 3-neck RB flask. The heel was washed with 20 ml THF and transferred to a flask for use in Example III(a). The reaction is illustrated by Equation 2:

Equation 2

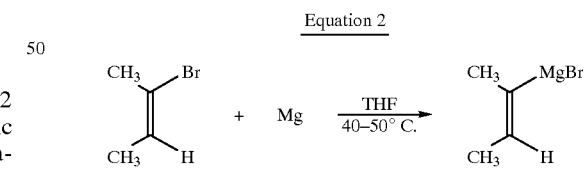

The Equation 2 reaction occurs in the presence of from about 1% to about 10% stoichiometric excess of magnesium is preferably conducted with a 5% excess of magnesium at a temperature of 40° C. to 50° C. to minimize formation of dimers of 2-bromo-2-butane. Near 100% conversion is achieved in about two to seven hours. The reaction may be conducted in any non-interfering solvent. Ether solvents, e.g., THF, are preferred.

Step 3: Conversion of 2-butenyl magnesium bromide into divinylcarbinol by reaction with ethyl formate and acetic acid.

A first phase of this preferably one pot conversion is illustrated by Example III(a). A second phase is illustrated by Example III(b).

Example III(a) (First Phase)

A flask containing 2-butenyl magnesium bromide in solution in THF from Example II was cooled to −10° C. Ethyl formate (37 g, 0.5 mol) was slowly added while maintaining temperature below 10° C. (1–2 hours). The mixture was stirred for 30 minutes. The reaction mixture contains 1,2,4,5-divinyl-3-carbinol (divinylcarbinol) magnesium bromide. This reaction is illustrated by Equation 3(a):

EQUATION 3(a)

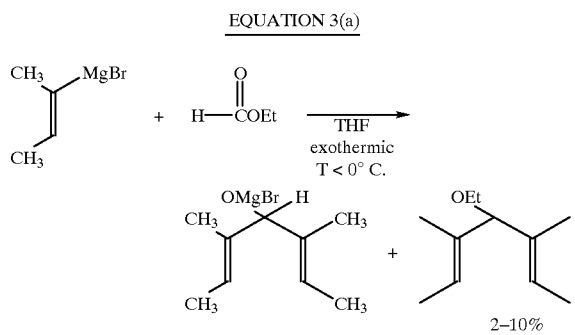

The Equation 3(a), first phase, reaction is preferably conducted at a temperature of from −10° C. to 10° C. for a time period of 0.5 hour to one hour. Any alkyl formate having 2 to 5 carbon atoms may be used in lieu of ethyl formate. The alkyl formate is preferably used in 0.5% to 2% stoichiometric excess. In the preferred practice of the invention, the same solvent, e.g., THF, is used in Steps 2 and 3(a). Any non-interfering solvent, e.g., ethyl ether, may be used.

In a second phase, the divinylcarbinol magnesium bromide first phase product is reacted with aqueous acetic acid preferably in the same pot to produce divinylcarbinol as illustrated by Example III(b).

Example III(b) (Second Phase)

20% aqueous AcOH (360 g, 360 ml) was slowly added to the Example III(a) reaction mixture while maintaining the temperature below 35° C. The mixture was stirred out for 15 minutes and allowed to separate for 15 minutes into an aqueous layer and an organic divinylcarbinol containing product layer. The aqueous layer was separated to remove magnesium salts and acetic acid. The organic layer was washed with 5% aqueous $Na_2CO_3$ and dried with $Na_2SO_4$ (2 g). The solids were removed by filtration. To recover the divinylcarbinol, the filtrate was distilled initially at atmospheric pressure and then under reduced pressure up to 70° C. pot temperature. This reaction is illustrated by Equation 3(b):

Equation 3(b)

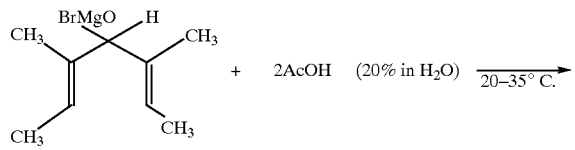

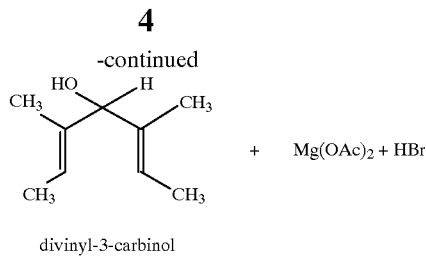

divinyl-3-carbinol

The Equation 3(b) reaction may be conducted with any acid of formula R-COOH in which R is a 1 to 5 carbon atom alkyl group at a temperature of from 20° C. to 35° C. for a time period of 10 to 20 minutes. The acid reactant is preferably used in about 10% excess with respect to the Equation 3(a) butenyl Grignard precursor.

Steps 2, 3(a) and 3(b) provide the overall divinylcarbinol yield 80% to 90% from 2-bromo-2-butene.

Step 4: Conversion of the Step 3 Divinylcarbinol Product to TMCp.

Example IV

The divinylcarbinol product of Example III(b) was distilled to remove residual THF. 425 ml ether and 10% HCl (200 ml) were added. The mixture was stirred at 20° C. for 2–4 hours until gas chromatography indicates that the reaction is complete. The reaction mixture was settled for 5 minutes. An organic layer and an aqueous layer formed. The organic layer which contained TMCp was separated, filtered to remove solids, and dried with $Na_2SO_4$ (2 g). The ether was removed by distillation. The neat, crude TMCp product is treated with 50% aqueous NaOH and heated to reflux to remove chlorotetramethylcyclopentene and NaBr.

The crude TMCp was distilled under 10–20 mm vacuum at a temperature of 50° C. to 85° C. The distillate was dried with 2 g $Na_2SO_4$ and filtered. The TMCp yield based on the divinylcarbinol was 75% to 85%. This reaction is illustrated by Equation 4:

Equation 4

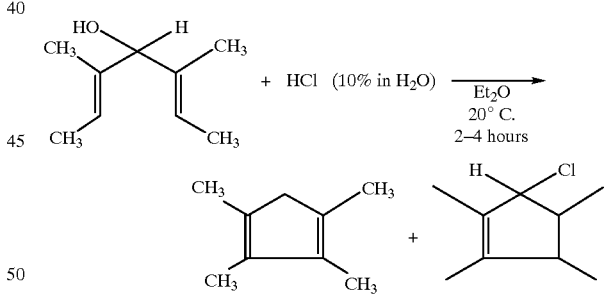

The divinylcarbinol used in the Equation 4 reaction should contain no more than about 5% by weight of THF. Preferably, the divinylcarbinol is substantially free of THF. The concentration of aqueous HCl may be from 5% to 20%. Acids, other than HCl, including $H_3PO_4$, $H_2SO_4$, and p-toluene sulfonic acid (PTSA), may be used in functionally equivalent concentrations.

II. PILOT PLANT EXEMPLIFICATION

Practice of the invention to produce a pilot plant batch generally parallels laboratory examples I to IV.

Production of 2-Bromo-2-Butene

Pilot Plant Process Description

Methanol is fed into solid sodium hydroxide. 2,3-dibromobutane is fed into the resulting slurry. A 5% hydrochloric acid solution is fed in and agitated. The resulting two-phase mixture is agitated, settled, and the lower product layer is separated off to another vessel. The organic layer is washed with a sodium bicarbonate solution, and the resulting lower aqueous layer is separated to another vessel. Sodium sulfate is added, and the resulting slurry is filtered to drums.

Pilot Plant Reaction 41.6 kg (1,040 moles) of solid sodium hydroxide is charged to a clean, dry nitrogen-purged chilled jacketed first reaction vessel fitted with a condenser. 112.6 kg of methanol is fed with agitation into the vessel with the condenser set at full reflux return. The initial 25 kg of methanol is charged at a moderate rate with full cooling on the vessel. The reaction is permitted to exotherm to 40° C.–50° C. Methanol feed is resumed when the vessel temperature begins to drop.

6.5 Kg of 2,3-dibromobutane is fed into the vessel. The exotherm is controlled in the range of 45° C.–50° C. After the initial exotherm, 187.9 kg (900 moles) of 2,3-dibromobutane is fed into the reaction vessel over a time period of about 1 hour with the temperature maintained in the range of 45° C.–50° C. After completion of the 2,3-dibromobutane addition, the reaction mixture is agitated for about 1 hour at 45° C.–50° C. and cooled to a temperature of less than 40° C.

194.3 kg of water and thereafter 31 kg of HCl is fed with agitation into the second reaction vessel.

The contents of the second reaction vessel are fed to the reaction mixture in the first reaction vessel with full jacket cooling at a pot temperature of 30° C.–35° C. The reaction mixture in the first reaction vessel is then agitated for 30 minutes and allowed to settle. The mixture forms two layers. The lower organic (2-bromo-2-butene product) layer is transferred to a clean, dry, nitrogen-purged vessel and dried over sodium sulfate.

Production of Divinylcarbinol in THF

Pilot Plant Process Description 2-bromo-2-butene is added to a slurry of magnesium in THF to form a solution of 2-butenyl-2-magnesium bromide, 2M in THF. The reaction is exothermic and is started and run under nitrogen at 43–48° C. The product is agitated 2 hours after the reaction is complete. The resulting product is hot filtered to another vessel. The heel is washed using THF. Ethyl formate is fed with vigorous exotherm to the solution of 2-bromo-2-butenylmagnesium bromide in THF using the chiller. The mixture is agitated, and acetic acid is fed in. The aqueous layer is separated. The organic is washed with soda ash solution, and dried using sodium sulfate. The slurry is filtered to drums.

Pilot Plant Reaction 1080 kg of dry THF is charged to a first, clean, dry, nitrogen-purged reaction vessel. 84.6 kg of magnesium are charged to the nitrogen-blanketed THF in the first reaction vessel. 40.5 kg of 2-bromo-2-butene as produced in reaction 1 are charged to the first reaction vessel with agitation until a reaction (reaction 2) exotherm is observed. The exotherm is maintained at 43° C.–48° C. and <10 psig pot pressure. The Grignard couples at >50° C. The Grignard reaction mixture is agitated for 30 minutes after the exotherm is observed. After the Grignard reaction is evidenced by the exotherm, 367.7 kg of 2-bromo-2-butene is fed into the reaction vessel at a rate that accommodates a temperature of 43° C.–48° C. and a pot pressure of <15 psig. Upon completion of the 2-bromo-2-butene feed, the reaction mixture is stirred at 43° C.–48° C., and then cooled under 2–5 psig regulated nitrogen to 35° C.–40° C.

106.7 kg of ethyl formate is fed with agitation into a second reaction vessel, chilled to –40° C. The pot temperature is maintained in the range of –10° C. to 0° C. during the ethyl formate feed. Upon completion of the feed, the pot temperature is slowly raised to 10° C.–15° C. over a time period of 1 hour.

A solution of 248 kg of glacial acetic acid in 1000 liters of water is fed into the second reaction vessel slowly over a time period of 15 minutes with full cooling to maintain the pot temperature at <40° C. Upon completion of the acetic acid addition, the reaction mixture is agitated for 15 minutes 15 30° C.–35° C. The lower, aqueous layer is separated.

The contents of the first reaction vessel are transferred to the second reaction vessel. 35.4 kg of diethyl ether are added to the second reaction vessel with agitation. 50% aqueous sodium hydroxide is added incrementally at a pot temperature of <40° C. to neutralize the content of the second reaction vessel to a pH of 6–8. The neutralization reaction mixture contains 3,5-dimethyl-2,5-heptadiene-4-ol (divinylcarbinol) (see reaction 3) which is separated and dried over $Na_2SO_4$.

TMCp from Divinylcarbinol

Pilot Plant Process Description

Divinylcarbinol in THF from reaction 3 is charged to a vessel. THF is removed by atmospheric distillation, followed by rough pump vacuum. Ether is added back. Aqueous and organic layers are formed. A dilute hydrochloric acid solution is fed into the organic layer to neutralize residual NaOH from the divinylcarbinol synthesis reaction and to dissolve NaBr. The mixture is agitated until the cyclodehydration reaction is complete. The lower aqueous layer is separated. A 33% sodium hydroxide solution is added to the organic layer. The mixture is heated to distill ether and refluxed. The aqueous layer is removed. The organic layer is dried using sodium sulfate. The slurry is filtered to another vessel. Fractional distillation yields the final TMCp product in high purity. The final fractions are blended and treated with sodium sulfate.

Pilot Plant Reaction (i) THF removal—24 kg of 80% divinylcarbinol in THF from the preceding step is charged to a nitrogen-purged vessel. The THF content is reduced by distillation to <5%. The residual substantially THF free divinylcarbinol is cooled to 20° C.–25° C.

(ii) Cyclodehydration—A vessel containing the substantially THF-free divinylcarbinol from (i) is charged with 444 kg of diethyl ether.

A solution of 282.8 kg of water and 107.2 kg of HCl was prepared in a separate vessel. The HCl solution was fed into the vessel containing divinylcarbinol and ethyl ether with cooling and agitation at a maintained pot temperature of 20° C.–25° C. The upper, product layer is separated and washed with 50% aqueous sodium hydroxide to remove chlorotetramethylcyclopentene and NaBr. A lower aqueous layer is separated. Solvents including diethyl ether are removed by distillation from the separated upper TMCp product layer. The residual TMCp product is dried over sodium sulfate.

The invention as described yields tetramethylcyclopentadiene (TMCp) from 2,3-dibromobutane. The invention generally includes the use of 2,3-dibromoalkanes to produce 1,5-dimethyl-2,4-alkyl cyclopentadiene. Preferred 2,3-dibromoalkanes have five to ten carbon atoms. One aspect of this embodiment of the invention is generally indicated by the equation

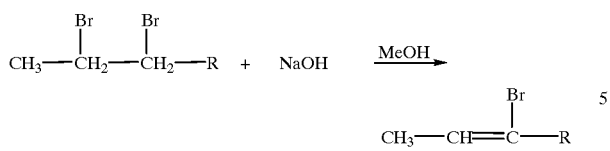

in which R may have 3 to 7 carbon atoms.

We claim:

1. The method which comprises:
   (i) reacting 2-bromo-2-butene with magnesium in a non-interfering solvent,
      wherein a first reaction mixture containing 2-butene magnesium bromide, magnesium and said non-interfering solvent;
   (ii) adding an alkyl formate

   (R = $C_1$–$C_6$ alkyl)

to said first reaction mixture,
      wherein said alkyl formate reacts with said 2-butene magnesium bromide in said first reaction mixture to produce a second reaction mixture containing a compound of formula

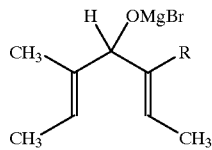

and
   (iii) adding an aqueous acid of formula

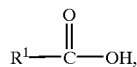

wherein $R^1$ is a two to six carbon atom alkyl group to said second reaction mixture,
      wherein a third reaction mixture containing 3,5-dimethyl-2,5-heptadiene-4-ol in said solvent is produced.

2. The of method of claim 1 further comprising
   (iv) removing said solvent from said third reaction mixture,
      wherein substantially solvent-free 3,5-dimethyl-2,5-heptadiene-4-ol is produced; and
   (v) treating said substantially solvent-free 3,5-dimethyl-2,5-heptadiene 4-ol with a hydrochloric acid,
      wherein a fourth reaction mixture containing tetramethyl cyclopentadiene is produced.

3. A method which comprises:
   (i) reacting 2-bromo-2-butene with magnesium
      wherein said reacting occurs in the presence of from about 1% to about 10% stoichiometric excess of magnesium and in the presence of tetrahydrofuran at a temperature of from about 40° C. to about 50° C.; and
      wherein a first reaction mixture containing 2-butene magnesium bromide, magnesium and tetrahydrofuran is produced;
   (ii) adding ethyl formate to said first reaction mixture at a temperature of from about –10° C. to about 10° C.
      wherein said ethyl formate reacts with said 2 butene magnesium bromide in said first reaction mixture to produce a second reaction mixture containing a compound of formula:

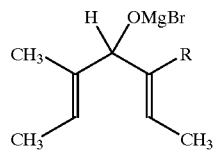

and
   (iii) adding aqueous acetic acid to said second reaction mixture
      wherein a third reaction mixture containing 3,5-dimethyl-2,5-heptadiene-4-ol, tetrahydrofuran and magnesium acetate is produced.

4. A method which comprises:
   (i) reacting 2-bromo-2-butene with magnesium
      wherein said reacting occurs in the presence of from about 1% to about 10% stoichiometric excess of magnesium and in the presence of tetrahydrofuran at a temperature of from about 40° C. to about 50° C.; and
      wherein a first reaction mixture containing 2-buteno magnesium bromide, magnesium and tetrahydrofuran is produced;
   (ii) adding ethyl formate to said first reaction mixture at a temperature of from about –10° C. to about 10° C.
      wherein said ethyl formate reacts with said 2-butene magnesium bromide in said first reaction mixture to produce a second reaction mixture containing a compound of formula:

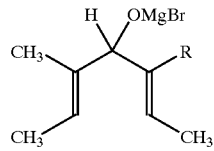

(iii) adding aqueous acetic acid to said second reaction mixture
      wherein a third reaction mixture containing 3,5-dimethyl-2,5-heptadiene-4-ol, tetrahydrofuran and magnesium acetate is produced;
   (iv) substantially completely removing tetrahydrofuran from said step (iii) third reaction mixture
      wherein substantially tetrahydrofuran free 3,5-dimethyl-2,5-heptadiene-4-ol is produced; and
   (v) combining said substantially tetrahydrofuran free 3,5-dimethyl-2,5-heptadiene-4-ol from step (iv) with aqueous hydrochloric acid and ethyl ether
      wherein a fourth reaction mixture containing chlorotetramethylcyclopentene, tetramethylcyclopentadiene and ethyl ether is produce.

5. The method of further claim 4 comprising steps (vi) to (ix):
   (vi) separating the mixture of said tetramethylcyclopentadiene and ethyl ether from said fourth reaction mixture,
   (vii) removing ethyl ether from said mixture with tetramethylcyclopentadiene separated in step (vi), wherein a tetramethylcyclopentadiene product substantially free of ethyl ether is produced; and (viii) treating said substantially ethyl ether free tetramethylcyclopentadiene product of step (vii) with aqueous alkali metal hydroxide
wherein a fifth reaction mixture having an aqueous phase and an organic phase containing tetramethylcyclopentadiene is produced; and (ix) separating and drying said step (viii) organic phase.

6. The method, of claim 4
wherein the aqueous hydrochloric acid utilized in step (v) is about 10% by weight aqueous hydrochloric acid.

7. The method of claim 3 wherein said step (i) 2-bromo-2-butene is produced by reacting 2,3-dibromobutane with methanolic sodium hydroxide.

8. The method of claim 3 wherein said step (i) 2-bromo-2-butene is produced by reacting 2,3-dibromobutane with an aqueous alkali metal hydroxide in the presence of a benzyl alkyl ammonium chloride.

9. A method which comprises:

(i) converting 2-bromo-2-butene to 3,5-dimethyl-2,5-heptadiene-4-ol, and (ii) converting said step (i) 3,5-dimethyl-2,5-heptadiene-4-ol to tetramethylcyclopentadiene.

10. The method of claim 9 wherein said converting step (ii) is accomplished by combining said step (i) 3,5-dimethyl-2,5-heptadiene-4-ol with aqueous hydrochloric acid and ethyl ether.

11. The method of claim 9 wherein said converting step (i) is accomplished by:

(i) reacting ethyl formate with 2-butene magnesium bromide in tetrahydrofuran,
wherein a first reaction mixture is produced;

(ii) removing tetrahydrofuran from said first reaction mixture produced in step (i), and (iii) combining the step (ii) tetrahydrofuran-free first reaction mixture with aqueous hydrochloric acid and ethyl ether,
wherein a second reaction mixture containing tetramethylcyclopentadiene is produced.

* * * * *

UNITED STATES PATENT AND TRADEMARK OFFICE
CERTIFICATE OF CORRECTION

PATENT NO.    : 6,388,151 B1
DATED         : May 14, 2002
INVENTOR(S)   : Jeffrey M. Sullivan and Richard D. Crawford It is certified that error appears in the above-identified patent and that said Letters Patent is hereby corrected as shown below:

<u>Column 7,</u>
Line 5, after "solvent", insert -- is produced --.

Signed and Sealed this

Thirtieth Day of September, 2003

JAMES E. ROGAN
*Director of the United States Patent and Trademark Office*